United States Patent [19]

Alig et al.

[11] Patent Number: 5,017,619
[45] Date of Patent: May 21, 1991

[54] PHENETHANOLAMINE DERIVATIVES

[75] Inventors: Leo Alig, Kaiseraugst; Marcel Müller, Frenkendorf, both of Switzerland

[73] Assignee: Hoffmann-La Roche Inc., Nutley, N.J.

[21] Appl. No.: 285,269

[22] Filed: Dec. 16, 1988

Related U.S. Application Data

[63] Continuation of Ser. No. 849,594, Apr. 8, 1986, abandoned.

[30] Foreign Application Priority Data

Apr. 16, 1985 [CH] Switzerland ............... 1607/85
Feb. 14, 1986 [CH] Switzerland ............... 599/86

[51] Int. Cl.$^5$ ............... A61K 31/135; C07C 215/04; C07C 215/06
[52] U.S. Cl. ............... 514/653; 514/237.5; 514/255; 514/330; 514/423; 514/512; 514/533; 514/539; 514/546; 514/551; 514/564; 514/567; 514/620; 514/909; 514/910; 544/162; 544/389; 544/391; 546/226; 548/530; 548/531
[58] Field of Search ............... 514/653, 909, 910, ; 564/361, 363, 364, 368, 374, 165; 544/162, 389, 391; 546/226; 548/530, 531; 558/275; 560/21, 42, 164, 251, 252; 562/437, 457

[56] References Cited

U.S. PATENT DOCUMENTS

| | | | |
|---|---|---|---|
| 3,152,173 | 10/1964 | Ehrhart et al. ............... | 564/361 X |
| 3,553,266 | 1/1971 | Bruce ............... | 564/363 |
| 3,577,462 | 5/1971 | Bruce ............... | 564/363 |
| 3,706,764 | 12/1972 | Nakanishi et al. ............... | 564/364 X |
| 3,911,016 | 10/1975 | Klingler et al. ............... | 564/381 |
| 4,396,627 | 8/1983 | Ainsworth et al. ............... | 514/533 |
| 4,585,796 | 4/1986 | Alig et al. ............... | 514/620 |

FOREIGN PATENT DOCUMENTS

0164700 6/1985 European Pat. Off. .
998288 7/1965 United Kingdom .
1109924 11/1966 United Kingdom .
8400956 3/1984 World Int. Prop. O. .

*Primary Examiner*—Richard L. Raymond
*Attorney, Agent, or Firm*—George M. Gould; William H. Epstein; Bruce A. Pokras

[57] ABSTRACT

The invention is directed to phenethanolamine derivatives and their pharmaceutically compatible salts, having the formula

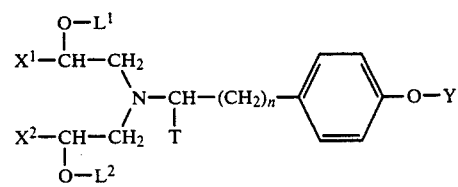

wherein n is the number 1 or 2; $L^1$ and $L^2$ are hydrogen, $C_{1-3}$-(alkyl)carbonyl or $C_{1-3}$(alkoxy) carbonyl; T is hydrogen or methyl; $X^1$ and $X^2$ are phenyl or phenyl which is monosubstituted in the m-position by Br, Cl, F, $CF_3$ and $NO_2$; Y is $-(CH_2)_{1-6}-O-G$, $-(CH_2)_{1-6}-CH=CH-C(O)-Z$, $-C(O)-Z$ or $-CH(COOR'')_2$; G is $C_{1-4}$-alkyl, $C_{1-4}$-alkoxy-$C_{1-4}$-alkyl or $-(CH_2)_{1-4}-Q$; Q is phenoxy, phenyl, p-fluorophenyl or p-phenoxyphenyl; Z is a $-OR$ or $-N(R,R')$; R and R' are hydrogen or $C_{1-4}$-alkyl or R and R' together with the N-atom to which they are attached form a 5- or 6-membered saturated ring which optionally contains an O-atom or an additional N-atom; and R'' is $C_{1-4}$-alkyl.

The compounds of the invention have catabolic activity and can be used for the treatment of obesity and of diabetes mellitus or of conditions which are associated with an increased protein breakdown, or as feed additives for fattening animals.

34 Claims, No Drawings

PHENETHANOLAMINE DERIVATIVES

This is a continuation, division, of application Ser. No. 849,594 filed Apr, 8, 1986, now abandoned.

The present invention is concerned with novel phenethanolamine derivatives a process for their manufacture and pharmaceutical preparations based on these compounds.

DETAILED DESCRIPTION OF THE INVENTION

The phenethanolamine derivatives in accordance with the invention are compounds of the formula

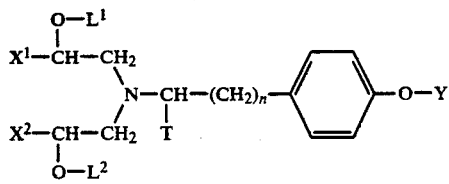   I wherein n is the number 1 or 2; $L^1$ and $L^2$ are hydrogen, $C_{1-3}$-(alkyl)carbonyl or $C_{1-3}$ (alkoxy)carbonyl; T is hydrogen or methyl; $X^1$ and $X^2$ are phenyl or phenyl which is monosubstituted in the m-position by Br, Cl, F, $CF_3$ or $NO_2$; Y is $-(CH_2)_{1-6}-O-G$, $-(CH_2)_{1-6}-CH=CH-C(O)-Z$, $-C(O)-Z$ or $-CH(COOR'')_2$; G is $C_{1-4}$-alkyl, $C_{1-4}$-alkoxy-$C_{1-4}$-alkyl or $-(CH_2)_{1-4}-Q$; Q is phenoxy, phenyl, p-fluorophenyl or p-phenoxyphenyl; Z is a -OR or -N(R,R'); R and R' are hydrogen or $C_{1-4}$-alkyl or R and R' together with the N-atom to which they are attached form a 5- or 6-membered saturated ring which optionally contains an O-atom or an additional N-atom; and R'' is $C_{1-4}$-alkyl; as well as the physiologically compatible salts thereof.

Alkyl, alkoxy and alkanoyl groups can be straight-chain or branched; examples are methyl, ethyl, propyl, isopropyl, n-butyl and isobutyl; methoxy, ethoxy, propoxy, isopropoxy, butoxy and isobutoxy; and acetyl, propionyl and butyryl, respectively. Examples of 5- or 6- membered saturated heterocyclic rings formed when R and $R^1$ are taken together with the nitrogen in the group -N(R, $R^1$), are pyrrolidine, piperidine, piperazine and morpholine.

The compounds of formula I form salts with acids and these salts are also an object of the invention. Examples of such salts are salts with physiologically compatible mineral acids such as hydrochloric acid, hydrobromic acid, sulphuric acid, phosphoric acid; or with organic acids such as oxalic acid, methanesulphonic acid, acetic acid, propionic acid, citric acid, maleic acid, succinic acid, malic acid, fumaric acid, phenylacetic acid or salicylic acid. Carboxylic acids are formula I can exist as salts. Examples of such salts of alkali metal, alkaline earth metal, ammonium and ethanolammonium salts.

The compounds in accordance with the invention contain at least two asymmetric carbon atoms and can therefore exist as optically active enantiomers as diastereomers or as racemates.

The compounds of formula I in which G is $C_{1-4}$-alkoxyalkyl are preferred. Compounds of formula I in which n is the number 1 are also preferred, as are those in which $L^1$ and $L^2$ are acetyl, ethoxycarbonyl or especially hydrogen. Among the compounds in which T is methyl there are preferred those in which the C-atom to which the methyl group T is attached has the R-configuration. Further preferred compounds of formula I are those in which $X^1$ and $X^2$ are phenyl, m-fluorophenyl or especially m-chlorophenyl, especially those in which the C-atom to which $X^1$ is attached has the R-configuration and the C-atom to which $X^2$ is attached has the R- or S-configuration. Further preferred compounds of formula I are those in which Y is 2-methoxyethoxyethyl, 2-p-fluorophenethoxyethyl, 2-phenoxyethoxyethyl, p-phenoxybenzyloxyethyl, dimethylcarbamoyl, methoxycarbonylallyl, bis(methoxycarbonyl)methyl, ethoxycarbonyl or especially 2-phenethoxyethyl or 2-ethoxyethyl.

Especially preferred are the compounds of formula I in which n is the number 1; $L^1$ and $L^2$ are hydrogen; T is hydrogen or methyl; $X^1$ and $X^2$ are m-chlorophenyl and Y is 2-phenethoxyethyl or 2-ethoxyethyl, particularly those in which the C-atom to which $X^1$ is attached has the R-configuration and the C-atom to which $X^2$ is attached has the R- or S-configuration.

The compound
α,α'-[[[p-(2-ethoxyethoxy)phenethyl]imino]dimethylene]bis[(R)-m-chlorobenzyl alcohol]
is especially preferred.

Further examples of preferred compounds are:
α,α'-[[[(R)-α-Methyl-p-[2-(phenethoxy)ethoxy]-phenethyl]imino]dimethylene]bis[(R)-m-chlorobenzyl alcohol], (R)-m-chloro-α-[[[(S)-m-chloro-β-hydroxyphenethyl]-(R)-α-methyl-p-[2-(phenethoxy)ethoxy]-phenethyl]amino]methyl]benzyl alcohol, 3-chloro-α,α'-[[[(R)-p-(2-ethoxyethoxy)-α-methylphenethyl]imino]dimethylene]di-(R)-benzyl alcohol, (S)-m-chloro-α-[[[(R)-p-(2-ethoxyethoxy)-α-methylphenethyl][(R)-β-hydroxyphenethyl]amino]methyl]-benzyl alcohol, (R)-m-chloro-α-[[[(S)-m-chloro-β-hydroxyphenethyl]-[p-(2-ethoxyethoxy)phenethyl]amino]methyl]benzyl alcohol and (R)-m-chloro-α-[[[(S)-m-chloro-β-hydroxyphenethyl]-[p-(2-phenoxyethoxy)phenethyl]amino]methyl]benzyl alcohol.

The compounds in accordance with the invention can be prepared by
(a) etherifying a phenol corresponding to the phenol ether of formula I with an agent which introduces the group Y, or
(b) alkylating an amine of the formula

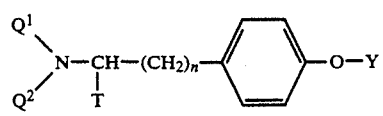   II wherein one of $Q^1$ and $Q^2$ is hydrogen and the other is hydrogen or a group Q of the formula

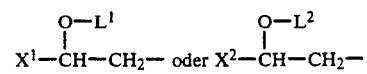

with an agent which introduces the group Q, or
(c) functionally modifying a reactive substituent present in a group Y of the reaction product, if desired esterifying one or both hydroxy groups in the β- position to the amine nitrogen atom and, if desired, converting a compound of formula I into a salt.

Examples of agents which introduce the group Y and which are used in variant (a) are compounds of the formula W-Y in which Y has the above significance and W is, for example, halogen, especially bromine or chlorine, or a sulphonate group, especially methanesulphonate. The reaction of W-Y with a phenol starting material corresponding to the phenol ether of formula I to be manufactured can be carried out in a manner known per se, e.g. in a solvent such as dimethyl sulphoxide, acetone, tetrahydrofuran or n-propanol in the presence of a base such as potassium hydroxide, potassium carbonate, potassium t-butylate or triethylamine, if desired under argon at a temperature up to the reflux temperature of the reaction mixture.

Examples of agents which introduce the group Q in variant (b) are epoxides of the formula

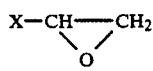   III or halides of the formula X—CHOH—CH$_2$—W or X—CO—CH$_2$—W in which X has the same significance as X$^1$ or X$^2$ and W is halogen, especially bromine or chlorine. Variant (b) can be carried out in a manner known per se, e.g. as described in European Patent Application 101069A1, conveniently while heating in a suitable solvent. Thus, the amine II and the epoxide are preferably reacted in an inert organic solvent, e.g. dimethyl sulphoxide (DMSO), acentonitrile, an ether such as tetrahydrofuran or dioxan or an alcohol such as ethanol, at a temperature between 60° C. and the boiling point of the reaction mixture. When the halide is used in place of the epoxide, the reaction can be carried out at a temperature up to 200 ° C. and in an inert organic solvent such as a halogenated hydrocarbon, e.g. chloroform. When a halide of the formula X—CO—CH$_2$—W is used, there is obtained an intermediate in which the keto group X—CO— must be reduced to the alcohol group X—CHOH—. This reaction can be carried out with a complex metal hydride such as NaBH$_4$ in a solvent such as an alkanol, e.g. methanol, at about 20°-30° C.

If desired, a reactive substituent which is present in a group Y of the reaction product of formula I can be functionally modified in a manner known per se. Thus, for example, an alkoxycarbonyl group —C(O)—Z, e.g. a methoxycarbonyl group, can be converted by means of an aqueous ammonia solution or be means of methylamine in a solvent such as ethanol into a carbamoyl or methylcarbamoyl group, respectively.

If desired, one or both hydroxy groups in the β-position to the amine nitrogen atom can be esterified in a manner known per se, e.g. with an alkanecarboxylic acid anhydride such as acetic anhydride in the presence of a base such as pyridine, to an alkanoyloxy or alkoxycarbonyloxy group —O—L$^1$ or —O—L$^2$, e.g. to an acetoxy or ethoxycarbonyloxy group.

The phenol starting materials which are used in variant (a) and which correspond to the phenol ethers of formula I can be prepared in a manner known per se, e.g. as described above in more detail in connection with variant (b), namely by alkylating a phenol corresponding to the phenol ether of formula II with an agent which introduces the group Q.

Thus, for the preparation of the phenol starting material in Example 1 hereinafter, 10.0 g of p-[(R)-2-aminopropyl]phenol and 8.8 g of R-styrene oxide in 300 ml of DMSO were heated to 100° C. for 24 hours. A further 17.5 g of R-styrene oxide were then added and the mixture was heated to 100° C. for a further 24 hours. The solvent was then removed by evaporation in a high vacuum and the residue was chromatographed on 1 kg of silica gel with chloroform/n-propanol/sat. NH$_3$ (1000:5:0.2). The fractions which were uniform according to thin-layer chromatography were combined. There were obtained 13 g of amorphous p-[(R)-2-[bis[(R)-β-hydroxyphenethyl]amino]propyl]phenol, [α 20/D= −76° (c=1.0 in methanol), ε$_{226}$=10180.

The following phenol starting materials were obtained in analogy thereto:

From tyramine and styrene oxide there was obtained pure, amorphous α,α'-[[(p-hydroxyphenethyl)imino]dimethylene]di-(R)-benzyl alcohol, [α]20/D= −53° (c=1.0 in methanol), the phenol starting material in Example 2f, from p-[(R)-2-aminopropyl]phenol and m-chloro-styrene oxide there was obtained p-[(R)-2-[bis[(R,S)-β-hydroxy-(3-chlorophenethyl)]amino]propyl]phenol, [α]20/D= −46° (c=0.5 in methanol), the phenol starting material in Example 2g, from p-[(R)-2-aminopropyl]phenol and m-trifluoromethyl-styrene oxide there was obtained α,α'-[[[(R)-p-hydroxy-α-methylphenethyl]imino]-dimethylene]bis[m-(trifluoromethyl)benzyl alcohol], [α]20/D= −29° (c=1.0 in methanol), the phenol starting material in Example 2h, from p-((R)-2-aminopropyl]phenol and m-nitro-styrene oxide there was obtained amorphous α,α'-[[[(R)-p-hydroxy-α-methylphenethyl]imino]dimethylene]bis[(RS)-m-nitrobenzyl alcohol, the phenol starting material in Example 2i, from p-[(R)-2-[[(R)-β-hydroxyphenethyl]amino]-propyl]phenol and (S)-styrene oxide there was obtained pure, amorphous (R)-α-[[[(R)-p-hydroxy-α-methylphenethyl][(S)-β-hydroxyphenethyl]amino]methyl]benzyl alcohol, [α]20/D= −66° (c=1.0 in methanol), the phenol starting material in Example 7, from tyramine and m-chloro-styrene oxide there was obtained pure, amorphous α,α'-[[(p-hydroxyphenethyl)-imino]dimethylene] bis[(RS)-m-chlorobenzyl alcohol], the phenol starting material in Examples 8a and 8b, from tyramine and m-bromo-styrene oxide there was obtained amorphous α,α'-[[(p-hydroxyphenethyl)imino]dimethylene]bis[(RS)-m-bromobenzyl alcohol], the phenol starting material in Example 8c, from tyramine and (R)-m-chloro-styrene oxide there was obtained amorphous α,α'-[[(p-hydroxyphenethyl)imino]dimethylene]bis[(R)-m-chlorobenzyl alcohol], [α]20/D= −22° (c=0.8 in methanol), the phenol starting material in Example 8d.

from p-[(R)-2-aminopropyl)phenol and m-bromo-styrene oxide there was obtained amorphous α,α'-[[[(R)-p-hydroxy-α-methylphenethyl]imino]dimethylene]bis[(RS)-m-bromobenzyl alcohol], [α]20/D= −30° (c=1.0 in methanol), the phenol starting material in Example 9a, from p-[(R)-2-[[(R)-β-hydroxyphenethyl]amino]-propyl]phenol and m-chloro-styrene oxide there was obtained pure, amorphous (RS)-m-chloro-α-[[[(R)-p-hydroxy-α-methylphenethyl][(R)-β-hydroxyphenethyl]amino]methyl]benzyl alcohol, the phenol starting material in Example 10a, from p-[(R)-2-aminopropyl]phenol and m-fluoro-styrene oxide the p-[(R)-2-[bis[(RS)-β-hydroxy-(3-fluorophenethyl)]amino]propyl]phenol; amorphous, $[\alpha]20/D = -48°$ (c=0.5 in methanol), the phenol starting material in Example 10c, from p-[(S)-2-aminopropyl]phenol and m-chloro-styrene oxide there was obtained amorphous p-[(S)-2-[bis[(R,S)-β-hydroxy-(3-chlorophenethyl)]amino]-propyl]phenol, $[\alpha]20/D = +40°$ (c=1.0 in methanol), the phenol starting material in Example 10d.

The amine starting materials of formula II can also be prepared in a manner known per se, e.g. starting from the phenols corresponding to the phenol ethers of formula II in which $Q^1$ and $Q^2$ are hydrogen by monoalkylation with an agent which introduces a group Q and etherification of the resulting phenol.

Thus, for the preparation of the amine starting material in Example 11 hereinafter, tyramine was reacted with (R)-m-chloro-styrene oxide in DMSO while heating to give (R)-m-chloro-[[(p-hydroxyphenethyl)amino]methyl]benzyl alcohol and the latter was etherified by reaction with 2-ethoxyethylmethanesulphonate to give (R)-m-chloro-α-[[[(p-(2-ethoxyethoxy)phenethyl]amino]methyl]benzyl alcohol, $[\alpha]20/D = -20°$ (c=0.5 in methanol).

In analogy thereto there was obtained (R)-m-chloro-α-[[[p-[2-(phenethoxy)ethoxy]phenethyl]amino]methyl]benzyl alcohol, $[\alpha]20/D = -17°$ (c=0.5 in methanol), the amine starting material in Example 12.

The phenethanolamine derivatives in accordance with the invention can be used as active substances in pharmaceutical preparations for the treatment of obesity and/or of diabetes mellitus, especially of obese adult diabetics. In an animal experiment an increased catabolism, primarily of fat, has been observed upon the administration of the phenethanolamine derivatives in accordance with the invention. Furthermore, it has been observed that the phenethanolamine derivatives in accordance with the invention stimulate the formation of brown adipose tissue in rats and obese-hyperglycaemic mice. It is known that defects of the brown adipose tissue play a substantial role in the origin of obesity. In obese-hyperglycaemic mice and in streptozotocin-diabetic rats the phenethanolamine derivatives in accordance with the invention have a pronounced antidiabetic effect, in that they have hypoglycaemic activity and reduce glycosuria. The phenethanolamine derivatives in accordance with the invention exhibit only a slight activity on the working of the heart and circulation. The dosage can amount to 0.5-1000 mg, preferably 2-200 mg, per day for an adult depending on the strength of activity of the individual compounds and on the individual requirements of the patients, whereby the dosage can be administered as a single dosage or in several dosages divided over the day.

In addition, in an animal experiment with the phenethanolamine derivatives in accordance with the invention an increase in the body protein content and a decrease in the fat content could be detected. The phenethanolamine derivatives in accordance with the invention therefore lead to an increase in the lean composition of the body at the expense of fat. Accordingly, the phenethanolamine derivatives in accordance with the invention can be used above all in human medicine for the treatment of conditions which are associated with high protein breakdown, e.g. in convalescence after an operation. In this case the dosages administered lie in the same range as in the treatment of obesity and/or of diabetes mellitus.

The phenethanolamine derivatives in accordance with the invention can also be used in the maintenance of fattening animals such as beef cattle, pigs, sheep and poultry. In this case the dosages administered and the dosage forms administered can be the same as in the case of vitamins. The phenethanolamine derivatives in accordance with the invention can also be used as feed additives in dosages of 0.01-100 mg/kg depending on the substance, kind of animal and age.

The pharmaceutical preparations contain the active substance together with a compatible pharmaceutical organic or inorganic carrier material such as e.g. water, gelatine, gum arabic, lactose, starch, magnesium stearate, talc, vegetable oils, polyalkylene glycols, Vaseline and the like. The pharmaceutical preparations are preferably administered orally, e.g. in the form of tablets, capsules, pills, powders, granulates, solutions, syrups, suspensions, elixirs and the like. The administration can, however, also be carried out parenterally, e.g. in the form of sterile solutions, suspensions or emulsions. The pharmaceutical preparations can be sterilized and/or can contain ingredients such as preserving agents, stabilizers, wetting agents, emulsifiers, salts for varying the osmotic pressure and buffer substances.

The activity of the novel compounds of formula I is evident from the following test results:

(1) Activity on oxygen consumption

Male albino rats weighing 160-180 g were placed in metabolic cages after fasting for 24 hours. The cages were ventilated with a constant 6 liter room air/minute which was equilibrated at a dew point of 11° C. Samples of the spent air were collected during periods of in each case 14 minutes after again equilbrating and the oxygen content and $CO_2$ content were analyzed. After an adaptation time of 4 hours the animals, divided into groups of 6, received either placebo (5% gum arabic) or the test substance (suspended in 5% gum arabic) per os. Thereafter, the determinations were carried out for a period of 12 hours. In Table I there is given the percentage of the average oxygen consumption after medication during the first 3 hours and the entire test duration (12 hours) of the oxygen consumption of the adaptation period, corresponding corrections for variations in the placebo group having been taken into consideration.

TABLE I

| Compound manufactured in Example No. | Dosage μM/kg | $O_2$ consumption % of value of the pre-period | |
|---|---|---|---|
| | | 1st-3rd hour | 1st-12th hour |
| 1 | 1 | 147 | 117 |
| 2a | 0.3 | 152 | 114 |
| 2b | 1 | 166 | 119 |
| 2c | 1 | 167 | 122 |
| 2e | 1 | 145 | 116 |
| 2f | 1 | 142 | 112 |
| 2g1 | 0.3 | 137 | 117 |
| 2g2 | 1 | 163 | 131 |
| 2g3 | 3 | 138 | 119 |
| 4 | 0.3 | 123 | 110 |
| 8d | 3 | 172 | 147 |
| 10a1 | 0.3 | 154 | 117 |
| 10a2 | 3 | 183 | 141 |
| 11 | 3 | 181 | 140 |
| 12a | 1 | 143 | 116 |

(2) Activity on urine glucose and blood glucose and the formation of brown adipose tissue Female hyperglycaemic fat mice were adapted to an amount of feed limited to 3 g/day/animal. The test compounds (suspended in 5% gum arabic) or placebo (5% gum arabic) were administered orally twice daily during 15 days. Urine was collected for 6 days a week and urine glucose was determined. Blood glucose and the weight of the interscapular brown adipose tissue were determined at the end of the test.

The test results are given in Table II as a percentage of the control value.

TABLE II

| Compound prepared in Example No. | Dosage μM/Kg per day | Urine glucose 1st week/ 2nd week | Blood glucose | Brown adipose tissue |
|---|---|---|---|---|
| 2f | 90 | 4.8%/0.3% | 34% | 163% |
|  | 9 | 43%/33% | 51% | 158% |
| 2g2 | 30 | 1.6%/0.6% | 33% | 144% |
|  | 3 | 17.7%/2.4% | 38% | 157% |

(3) Activity on the urine glucose of streptozotocin-diabetic rats

A diabetes was produced in female albino rats (weight 130–140 g) by the subcutaneous injection of streptozotocin (70 mg/kg). The diabetic animals were adapted to an amount of feed limited to 15 g/day/animal. The test compound (suspended in 5% gum arabic) or placebo (5% gum arabic) was administered orally twice daily. The urine was collected for 6 days a week and urine glucose was determined. The urine glucose excretion of the treated animals during the 2nd week of treatment is given in Table III as a percentage of the control value.

TABLE III

| Compound manufactured in Example No. | Dosage μM/kg per day | Urine glucose 2nd week % of controls |
|---|---|---|
| 2g2. | 90 | 68 |

The following Examples illustrate the invention in more detail.

EXAMPLE 1

186 mg of potassium hydroxide and 780 mg of 2-(phenethoxy)ethylmethanesulphonate were added to a solution of 520 mg of p-[(R)-2-[bis[(R)-β-hydroxyphenethyl]amino]propyl]phenol in 7 ml n-propanol and the mixture was heated to 120° for 2 hours. For the working-up, the mixture was poured on to ice-water and extracted with ethyl acetate. The extract gave, after washing with water, drying with Na$_2$SO$_4$ and removal of the solvent by evaporation, 600 mg of a crude oil which, after chromatography on 40 g of silica gel with chloroform/n-propanol/aqueous NH$_3$ (1000:10:1), gave 340 mg of pure, amorphous α,α'-[[[(R)-α-methyl-p-[2-(phenethoxy)ethoxy]phenethyl]imino]dimethylene]di-(R)-benzyl alcohol. [α]20/D= −66° (c=1.0 in methanol); ε$_{225}$=14080.

EXAMPLE 2

Analogously to Example 1, (2a) using 2-ethoxyethylmethanesulphonate there was obtained α,α'-[[[(R)-p-(2-ethoxyethoxy)-α-methylphenethyl]imino]dimethylene]di-(R)-benzyl alcohol, amorphous, [α]20/D= −75° (c=0.3 in methanol), ε$_{223}$=11450, (2b) using 2-(2-methoxyethoxy)ethylmethanesulphonate there was obtained α,α'-[[[(R)-p-[2-methoxyethoxy)ethoxy]-60 -methylphenethyl]-imino]dimethylene]di-(R)-benzyl alcohol, amorphous, [α]20/D= −75° (c=0.5 in methanol), (2c) using 2-(p-fluorophenethoxy)ethylenemethanesulphonate there was obtained α,α'-[[(R)-α-methyl-p-[2-(4-fluorophenethoxy)-ethoxy]-phenethyl]imino]dimethylene]di-(R)-benzyl alcohol, [α]20/D= −63° (c=0.6 in methanol), (2d) using 2-(2-phenoxyethoxy)ethylmethanesulphonate there was obtained α,α'-[[[(R)-α-methyl-p-[2-(phenoxyethoxy)ethoxy]-phenethyl]imino]dimethylene]di-(R)-benzyl alcohol, [α]20/D= −58° (c=0.5 in methanol), (2e) using 2-(4-phenoxybenzyloxy)ethylmethanesulphonate there was obtained α,α'-[[[(R)-α-methyl-p-[2-[(p-phenoxybenzyl)oxy]ethoxy]phenethyl]imino]dimethylene]di-(R)-benzyl alcohol, amorphous, [α]20/D= −60° (c=0.5 in methanol), (2f) from αα'-[[(p-hydroxyphenethyl)imino]dimethylene]di-(R)-benzyl alcohol and 2-ethoxyethylmethanesulphonate there was obtained α,α'-[[[p-(2-ethoxyethoxy)phenethyl]imino]dimethylene]di-(R)-benzyl alcohol, amorphous, [α]20/D= −48° (c=0.5 in methanol), (2g) from p-[(R)-2-[bis[(R,S)-β-hydroxy-(3 -chlorophenethyl]amino]propyl]phenol and 2-(phenethoxy)ethylmethanesulphonate there were obtained 2g1. α,α'-[[[(R)-α-methyl-p-[2 -(phenethoxy)ethoxy]-phenethyl]imino]dimethylene]bis[(R)-m-chlorobenzyl alcohol], amorphous, [α]20/D= −44° (c=1.0 in methanol), 2g2. (R)-m-chloro-α-[[[(S)-m-chloro-β-hydroxyphenethyl][(R)-α-methyl-p-[2-phenethoxy)ethoxy]-phenethyl]amino]-methyl]benzyl alcohol], [α]20/D= −41° (c=0.4 in methanol), and 2g3. α,α'-[[[(R)-α-methyl-p-(2-phenethoxy)ethoxy]-phenethyl]imino]dimethylene]bis[(S)-m-chlorobenzyl acohol], amorphous, [α]20/D= −17° (c=1.0 in methanol), (2h) from α,α'-[[[(R)-p-hydroxy-α-methylphenethyl]imino]dimethylene]bis[m-(trifluoromethyl)benzyl alcohol] and 2-ethoxyethylmethanesulphonate there were obtained 2h1. α,α'-[[[(R)-p-(2-ethoxyethoxy)-α-methylphenethyl]imino]dimethylene]bis[(R)-m-(trifluoromethyl)-benzyl alcohol], amorphous, [α]20/D= −52° (c=0.2 in methanol), 2h2. (R)-α-[[[(R)-p -(2-ethoxyethoxy)-α-methylphenethyl][(S)-β-hydroxy-m-(trifluoromethyl)phenethyl]amino]methyl-m-(triflurormethyl)benzyl alcohol, amorphous, [α]20/D= −37° (c=0.4 in methanol), and 2h3. α,α'-[[[(R)-p-(2-ethoxyethoxy)-α-methylphenethyl]imino]dimethylene]bis[(S)-m-(trifluoromethyl)benzyl alcohol], amorphous, [α]20/D= −4.5° (c=1.2 in methanol), (2i) from α,α'-[[[(R)-p-hydroxy-α-methylphenethyl]imino]dimethylene)bis((RS)-m-nitrobenzyl alcohol and 2-ethoxyethanolmethanesulphonate there were obtained 2i1. α,α'-[[[(R)-p-(2-ethoxyethoxy)-α-methylphenethyl]imino]dimethylene]bis(R)-m-nitrobenzyl alcohol, amorphous, [α]20/D= −54° (c=1.0 in methanol), and 2i2. (R)-α-[[[(R)-p-(2-ethoxyethoxy)-α-methylphenethyl][(S)-β-hydroxy-m-nitrophenethyl]amino]methyl]m-nitrobenzyl alcohol, amorphous, [α]20/D= −43° (c=0.5 in methanol).

EXAMPLE 3

A mixture of 755mg of α,α'-[[(p-hydroxyphenethyl)imino]dimethylene]di-(R)-benzyl alcohol, 10 ml of tetrahydrofuran, 237 mg of dimethylcarbamoyl chloride, of 4-dimethylaminopyridine and 202 mg of triethylamine was heated to reflux under argon for 4 hours. For the working-up, the mixture was cooled, poured on to ice-water and extracted with methylene chloride. The extract was washed with NaCl solution, dried with $Na_2SO_4$ and evaporated. The residue was chromatographed on silica 9el. With chloroform/n-propanol/25% $NH_3$ (1000:5:0.5) there were eluted 510 mg of pure, amorphous p-[2-[bis[((R)-β-hydroxyphenethyl]amino]ethyl]phenyldimethylcarbamate, [α]20/D= −47° (c=0.5 in methanol).

EXAMPLE 4

A mixture of 500 mg of p-[(R)-2-[bis[(R)-β-hydroxyphenethyl]amino]propyl]phenol, 229 mg of methyl 4-bromo-2-butenoate, 72 mg of potassium hydroxide, a trace of potassium iodide and 50 ml of acetone was stirred at room temperature under argon for 4 hours. For the working-up, the mixture was poured on to ice-water and extracted with ethyl acetate. The organic extract was washed neutral with water, dried with $Na_2SO_4$ and evaporated in vacuo. After chromatography on silica gel with chloroform/propanol (99:1) the residue yielded 400 mg of pure, amorphous methyl 4-[p-[[(R)-2-[bis[(R)-β-hydroxyphenethyl]amino]propyl]-phenoxy]crotonate, [α]20/D= −70° (c=0.3 in methanol); $\epsilon_{203}=43270$.

EXAMPLE 5

783 mg of p-[(R)-2-[bis[(R)-β-hydroxyphenethyl]amino]propyl]phenol were dissolved in 40 ml of acetone and stirred at room temperature for 5 hours with 112 mg of powd. potassium hydroxide, 422 mg of dimethyl bromomalonate and a trace of potassium iodide. For the working-up, the mixture was poured on to ice-water and extracted with ethyl acetate. After removal of the solvent by evaporation and chromatography of the crude product on silica gel (toluene/ethyl acetate 5:1) there were obtained 450 mg of thin-layer chromatographically uniform, amorphous dimethyl [p-[(R)-2-[bis[(R)-β-hydroxyphenethyl]amino]propyl]-phenoxy]-malonate; [α]20/D= −58° (c=0.5 in methanol), $\epsilon_{224}=23600$.

EXAMPLE 6

(a) 1.17 g of p-[(R)-2-[bis[(R)-β-hydroxyphenethyl]amino]propyl]phenol were dissolved in 100 ml of acetone and stirred at room temperature for 10 hours with 357 mg of ethyl chloroformate, 177 mg of powd. potassium hydroxide and a trace of potassium iodide. Working-up with ethyl acetate as in Example 8 yielded 1.16 g of an oily crude product which was chromatographed on 100 g of silica gel with chloroform/n-propanol/aq. $NH_3$ (1000:10:1). The thin-layer chromatographically uniform fractions were combined. There were firstly eluted 280 mg of pure, amorphous p-[(R)-2-[[(R)-β-(ethoxycarbonyl)oxy]phenethyl][(R)-β-hydroxyphenethyl]amino]propyl]phenethyl carbonate; [α]20/D= −80° (c=0.5 in methanol).

(b) There were then eluted 380 mg of pure, amorphous p-[(R)-2-[bis[(R)-β-hydroxyphenethyl]amino]propyl]phenethyl carbonate: [α]20/D= −82° (c=0.3 in methanol).

EXAMPLE 7

Analogously to Example 1,
from (R)-α-[[[(R)-p-hydroxy-60-methylphenethyl][(S)-β-hydroxyphenethyl]amino]methyl]benzyl alcohol there was obtained
(R)-α-[[[(S)-β-hydroxyphenethyl][(R)-α-methyl-p-(2-phenethoxyethoxy)phenethyl]amino]methyl]benzyl alcohol, [α]20/D= −51° (c=0.5 in methanol).

EXAMPLE 8

Analogously to Example 2f,
(a) from α,α'-[[(p-hydroxyphenethyl)imino]dimethylene]bis[(RS)-m-chlorobenzyl alcohol] there was obtained
α,α'-[[[p-(2-ethoxyethoxy)phenethyl]imino]dimethylene]bis[(RS)-m -chlorobenzyl alcohol], IR bands at 3396, 1610, 1598, 1575, 1511, 1246, 1124, 1067, 897, 826, 786, 693 $cm^{-1}$, (b) from α,α'-[[(p -hydroxyphenethyl)imino]dimethylene]bis[(RS)-m-chlorobenzyl alcohol] and 2-(phenethoxy)ethylmethanesulphonate there was obtained
α,α'-[[[p-2-(phenethoxy)ethoxy]phenethyl]imino]-dimethylene]bis[(RS)-m-chlorobenzyl alcohol], IR bands at 3404, 1246, 1125, 1069, 826, 787, 749, 698 $cm^{-1}$, (c) from α,α'-[[(p-hydroxyphenethyl)imino]dimethylene]bis[(RS)-m-bromobenzyl alcohol] there was obtained
α,α'-[[[p-(2 -ethoxyethoxy)phenethyl]imino]dimethylene]bis[(RS)-m-bromobenzyl alcohol], IR bands at 3395, 2928, 2870, 1610, 1595, 1569, 1246, 1123, 1067, 784, 695 $cm^{-1}$, and (d) from α,α'-[[(p-hydroxyphenethyl)imino]dimethylene]bis[(R)-m-chlorobenzyl alcohol] there was obtained
α,α'-[[[p-(2-ethoxyethoxy)phenethyl]imino]dimethylene]bis[(R)-m-chlorobenzyl alcohol], [α]20/D= −21° (c=0.5 in methanol).

EXAMPLE 9

Analogously to Example 2g,
(a) from α,α'-[[[(R)-p-hydroxy-α-methylphenethyl]imino]dimethylene]bis[(RS)-m-bromobenzyl alcohol] there were obtained
1. α,α'-[[[(R)-α-methyl-p-[2-(phenethoxy)ethoxy]-phenethyl]imino]dimethylene]bis[(R)-m-bromobenzyl alcohol] [α]20/D= −42° (c=0.3 in methanol),
2. (R)-m-bromo-α-[[[(S)-m-bromo-β-hydroxyphenethyl][(R)-α-methyl-p-[(2-phenethoxy)ethoxy]-phenethyl]amino]methyl]benzyl alcohol, [α]20/D= −34° (c=0.5 in methanol), and
3. α,α'-[[[(R)-α-methyl-p-[2 -(phenethoxy)ethoxy]-phenethyl]imino]dimethylene]bis[(S)-m-bromobenzyl alcohol], [α]20/D= −17° (c=0.5 in methanol), (b) from α,α'-[[[(S)-p-hydroxy-α-methylphenethyl]imino]dimethylene]bis[(RS)-m-chlorobenzyl alcohol] there were obtained
1. α,α'-[[[(S)-α-methyl-p-[2-(phenethoxy)ethoxy]-phenethyl]imino]dimethylene]bis[(R)-m-chlorobenzyl alcohol, [α]20/D= +19° (c=0.4 in methanol), and 2. (R)-m-chloro-α-[[[(S)-m-chloro-β-hydroxyphenethyl][(S)-α-methyl-p-[(2-phenethoxy)ethoxy]phenethyl]amino]methyl]benzyl alcohol, [α]20/D = +45° (c=0.3 in methanol).

EXAMPLE 10

Analogously to Example 2h, (a) from (RS)-m-chloro-α-[[[(R)-p-hydroxy-α-methylphenethyl][(R)-β-hydroxyphenethyl]amino]methyl]benzyl alcohol there were obtained 1. 3-chloro-α,α'-[[[(R)-p-(2-ethoxyethoxy)-α-methylphenethyl]imino]dimethylene]di-(R)-benzyl alcohol, [α]20/D= −68° (c=0.9 in methanol), and
2. (S)-m-chloro-α-[[[(R)-p-(2-ethoxyethoxy)-α-methylphenethyl][(R)-β-hydroxyphenethyl]amino]methyl]benzyl alcohol, [α]20/D= −56° (c=1.0 in methanol), (b) from α,α'-[[[(R)-p-hydroxy-α-methylphenethyl]imino]dimethylene]bis[(RS)-m-chlorobenzyl alcohol] there were obtained 1. α,α'-[[[(R)-p-(2-ethoxyethoxy)-α-methylphenethyl]imino]dimethylene]bis[(R)-m-chlorobenzyl alcohol], [α]20/D= −59° (c=0.5 in methanol),
2. (R)-m-chloro-α-[[[(S)-m-chloro-62-hydroxyphenethyl][(R)-p-(2-ethoxyethoxy)-α-methylphenethyl]amino]methyl]benzyl alcohol, [α]20/D= −39° (c=0.4 in methanol), and
3. α,α'-[[[(R)-p-(2-ethoxyethoxy)-α-methylphenethyl]imino]dimethylene]bis[(S)-m-chlorobenzyl alcohol], [α]20/D= −14° (c=0.3 in methanol), (c) from p-[(R)-2-[bis[(RS)-β-hydroxy-(3-fluorophenethyl)]amino]propyl]phenol there were obtained 1. α,α'-[[[(R)-p-(2-ethoxyethoxy)-α-methylphenethyl]imino]dimethylene]bis[(R)-m-fluorobenzyl alcohol], [α]20/D= −73° (c=1.0 in methanol).
2. (R)-m-fluoro-α-[[[(S)-m-fluoro-β-hydroxyphenethyl][(R)-p-(2-ethoxyethoxy)-α-methylphenethyl]amino]methyl]benzyl alcohol, [α]20/D= −59° (c=1.0 in methanol), and
3. α,α'-[[[(R)-p-(2-ethoxyethoxy)-α-methylphenethyl]imino]dimethylene]bis[(S)-m-flurorbenzyl alcohol], [α]20/D= −16° (c=1.0 in methanol), (d) from p-[(S)-2-[bis[(RS)-β-hydroxy-(3-chlorophenethyl)]amino]propyl]phenol there were obtained 1. α,α'-[[[(S)-p-(2-ethoxyethoxy)-α-methylphenethyl]imino]dimethylene]bis[(S)-m-chlorobenzyl alcohol], [α]20/D= +57° (c=0.7 in methanol),
2. (R)-m-chloro-α-[[[(S)-m-chloro-β-hydroxyphenethyl][(S)-p-(2-ethoxyethoxy)-α-methylphenethyl]amino]methyl]benzyl alcohol, [α]20/D= +52° (c=0.5 in methanol), and
3. α,α'-[[[(S)-p-(2-ethoxyethoxy)-α-methylphenethyl]imino]dimethylene]bis[(R)-m-chlorobenzyl alcohol], [α]20/D= +23° (c=0.3 in methanol).

EXAMPLE 11

A solution of 1.15 g of (R)-m-chloro-α-[[[p-(2-ethoxyethoxy)phenethyl]amino]methyl]benzyl alcohol and 0.9 g of (S)-m-chloro-styrene oxide in 50 ml DMSO was heated to 100° for 20 hours. The reaction mixture was evaporated at 60° in a high vacuum and the residue was chromatographed on 150 g of silica gel. Using chloroform/n-propanol/sat. NH3 solution (1000;2:0.2) there was eluted 0.9 g of pure, amorphous (R)-m-chloro-α-[[[(S)-m-chloro-β-hydroxyphenethyl][p-(2-ethoxyethoxy)phenethyl]amino]methyl]benzyl alcohol, IR bands at 3396, 2928, 2871, 1598, 1575, 1511, 1246, 1124, 1066, 786, 693 cm⁻¹.

EXAMPLE 12

Analogously to Example 11, from (R)-m-chloro-α-[[[p-[2-(phenethoxy)ethoxy]phenethyl]amino]methyl]benzyl alcohol there was obtained (a) (R)-m-chloro-α-[[[(S)-m-chloro-β-hydroxyphenethyl]-[p-[2-(phenethoxy)ethoxy]phenethyl]amino]methyl]benzyl alcohol, IR bands at 3394, 1598, 1575, 1511, 1496, 1246, 1125, 1068, 894, 826, 786, 749, 698 cm⁻¹, and (b) using (R)-m-chloro-styrene oxide there was obtained α,α'-[[[p-[2-(phenethoxy)ethoxy]phenethyl]imino]dimethylene]bis[(R)-m-chlorobenzyl alcohol], [α]20/D= −17° (c=0.3 in methanol).

EXAMPLE 13

304 mg of (R)-m-chloro-α-[[[(S)-m-chloro-β-hydroxyphenethyl][(R)-α-methyl-p-[2-(phenethoxy)ethoxy]phenethyl]amino]methyl]benzyl alcohol and 45 mg of oxalic acid were dissolved in 2 ml of methanol. After the addition of 8 ml of diethyl ether there crystallized out 225 mg of pure oxalate of m.p. 134°–135°, [α]20/D= −19° (c=1.0 in methanol).

EXAMPLE 14

130 mg of α,α'-[[[p-(2-ethoxyethoxy)phenethyl]imino]dimethylene]bis[(R)-m-chlorobenzyl alcohol] and 29 mg of maleic acid were dissolved in 0.5 ml of methanol and subsequently treated with 5 ml of ether. The mixture was left to stand at room temperature for 20 hours and the precipitated crystals were filtered off under suction. There were obtained 77 mg of crystalline maleate, m.p. 116°–118°, [α]20/D= −44° (c=0.6 in methanol).

EXAMPLE 15

Tablets of the following composition are manufactured in the usual manner:

| | |
|---|---|
| Active substance of formula I, e.g. α,α'-[[[p-(2-ethoxyethoxy)phenethyl]imino]dimethylene]bis[(R)--m-chlorobenzyl alcohol] | 250 mg |
| Lactose | 200 mg |
| Maize starch | 300 mg |
| Maize starch paste | 50 mg |
| Calcium stearate | 5 mg |
| Dicalcium phosphate | 45 mg |

We claim:

1. A compound of the formula:

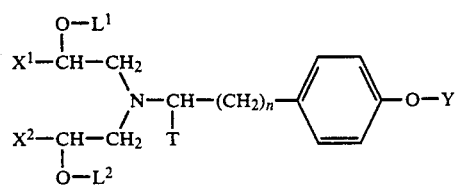

wherein n is the number 1 or 2; $L^1$ and $L^2$ are hydrogen, $C_{1-3}$-(alkyl)carbonyl or $C_{1-3}$ (alkoxy)carbonyl; T is hydrogen or methyl; $X^1$ and $X^2$ are phenyl or phenyl which is monosubstituted in the m-position by Br, Cl, F, CF3 or NO2; Y is —(CH2)1-6—O—G, —(CH2)1-6—CH=CH—C(O)—Z, —C(O)—Z or —CH- (COOR")$_2$; G is $C_{1-4}$-alkyl, $C_{1-4}$-alkoxy-$C_{1-4}$-alkyl or —(CH$_2$)$_{1-4}$—Q; Q is phenoxy, phenyl, p-fluorophenyl or p-phenoxyphenyl; Z is a -OR or -N(R,R'); R and R' are hydrogen or $C_{1-4}$-alkyl or R and R' together with the N-atom to which they are attached form a 5- or 6-membered saturated ring which optionally contains an O-atom or an additional N-atom; and R" is $C_{1-4}$-alkyl; as well as the physiologically compatible salts thereof.

2. A compound according to claim 1, in which G is $C_{1-4}$-alkoxyalkyl.

3. A compound according to claim 2, in which n is the number 1.

4. A compound according to claim 3, in which L$^1$ and L$^2$ are acetyl, ethoxycarbonyl or hydrogen.

5. A compound according to claim 4 wherein L$^1$ and L$^2$ are hydrogen.

6. A compound according to claim 4, in which T is methyl.

7. A compound according to claim 6, in which the C-atom to which the methyl group T is attached has the R-configuration.

8. A compound according to claim 6 in which X$^1$ and X$^2$ are phenyl, m-fluorophenyl or m-chlorophenyl.

9. A compound according to claim 8 in which the C-atom to which X$^1$ is attached has the R-configuration and the C-atom to which X$^2$ is attached has the R- or S-configuration.

10. A compound according to claim 9 wherein X$^1$ and X$^2$ are m-chlorophenyl.

11. A compound according to claim 8, in which Y is 2-methoxyethoxyethyl, 2-p-fluorophenethoxyethyl, 2-phenoxyethoxyathyl, p-phenoxybenzyloxyethyl, dimethylcarbamoyl, methoxycarbonylallyl, bis(methoxycarbonyl)-methyl, ethoxycarbonyl, 2-phenethoxyethyl or 2-ethoxyethyl.

12. A compound according to claim 11, wherein Y is 2-phenethoxyethyl or 2-ethoxyethyl.

13. A compound according to claim 1, in which n is the number 1; L$^1$ and L$^2$ are hydrogen; T is hydrogen or methyl; X$^1$ and X$^2$ are m-chlorophenyl and Y is 2-phenethoxyethyl or 2-ethoxy-ethyl, wherein the C-atom to which X$^1$ is attached has the R-configuration and the C-atom to which X$^2$ is attached has the R- or S-configuration.

14. A compound according to claim 1, which is α,α'-[[[p-(2-Ethoxyethoxy)phenethyl]imino]dimethylene]-bis[(R)-m-chlorobenzyl alcohol].

15. A compound according to claim 1 selected from the group consisting of:
 α,α'-[[[(R)-α-Methyl-p-[2-(phenethoxy)ethoxy]-phenethyl]imino]dimethylene]bis[(R)-m-chlorobenzyl alcohol],
 (R)-m-chloro-α-[[[(S)-m-chloro-β-hydroxyphenethyl]-(R)-α-methyl-p-[2-(phenethoxy)ethoxy]-phenethyl]amino]methyl]benzyl alcohol,
 3-chloro-α,α'-[[[(R)-p-(2-ethoxyethoxy)-α-methyl-phenethyl]imino]dimethylene]di-(R)-benzyl alcohol,
 (S)-m-chloro-α-[[[(R)-p-(2-ethoxyethoxy)-α-methyl-phenethyl][(R)-β-hydroxyphenethyl]amino]methyl]-benzyl alcohol,
 (R)-m-chloro-α-[[[(S)-m-chloro-β-hydroxyphenethyl][p-(2-ethoxyethoxy)phenethyl]amino]methyl]-benzyl alcohol and
 (R)-m-chloro-α-[[[(S)-m-chloro-β-hydroxyphenethyl][p-(2-phenethoxyethoxy)phenethyl]amino]-methyl]benzyl alcohol.

16. A pharmaceutical composition comprising a physiologically active compounde and a compatible pharmaceutical carrier, wherein said active compound has the formula $$\begin{array}{c} O-L^1 \\ | \\ X^1-CH-CH_2 \\ \phantom{X^1-CH}\diagdown \\ \phantom{X^1-CH-CH_2}N-CH-(CH_2)_n- \phantom{XX} -O-Y \\ \phantom{X^1-CH}\diagup \phantom{XXXX} | \\ X^2-CH-CH_2 \phantom{XX} T \\ | \\ O-L^2 \end{array} \quad I$$

wherein n is the number 1 or 2; L$^1$ and L$^2$ are hydrogen C$_{1-3}$-(alkyl) carbonyl or C$_{1-3}$(alkoxy)carbonyl; T is hydrogen or methyl; X$^1$ and X$^2$ are phenyl or phenyl which is monosubstituted in the m-position by Br Cl, F, CF$_3$ or NO$_2$; Y is —(CH$_2$)$_{1-6}$—O—G, —(CH$_2$)$_{1-6}$—CH=CH—C(O)—Z, —C(O)—Z or —CH(COOR")$_2$; G is C$_{1-4}$-alkyl, C$_{1-4}$-alkoxy-C$_{1-4}$-alkyl or —(CH$_2$)$_{1-4}$—Q; Q is phenoxy, phenyl, p-fluorophenyl or p-phenoxyphenyl; Z is a group OR or N(R,R'); and R' are hydrogen or C$_{1-4}$alkyl, or R and R' together with the N-atom to which they are attached form a 5- or 6-membered saturated ring which optionally contains an O-atom or an additional N-atom; R" is C$_{1-4}$-alkyl, as well as physiologically compatible salts thereof.

17. A composition according to claim 16, in which n is the number 1.

18. A composition according to claim 17, in which L$^1$ and L$^2$ are acetyl, ethoxycarbonyl or hydrogen.

19. A composition according to claim 18, wherein L$^1$ and L$^2$ are hydrogen.

20. A composition according to claim 18, in which T is methyl.

21. A composition according to claim 20, wherein the C-atom to which the methyl group T is attached has the R-configuration.

22. A composition according to claim 20, in which X$^1$ and X$^2$ are phenyl, m-fluorophenyl or m-chlorophenyl.

23. A composition according to claim 22, in which the c-atom to which X$^1$ is attached has the R-configuration and the C-atom to which X$^2$ is attached has the R- or S-configuration.

24. A composition according to claim 23, wherein X$^1$ and X$^2$ are m-chloro-phenyl.

25. A compound according to claim 22 wherein T is methyl and wherein the C-atom to which T is attached has the R-configuration and wherein the C-atom to which X$^1$ is attached has the R-configuration.

26. A composition according to claim 26, in which Y is 2-methoxyethoxyethyl, 2-p-fluorophenethoxyethyl, 2-phenoxyethoxyethyl, p-phenoxybenzyloxyethyl, dimethylcarbamoyl, methoxycarbonylallyl, bis(methoxycarbonyl)-methyl, ethoxycarbonyl or especially 2-phenethoxyethyl or 2-ethoxyethyl.

27. A composition according to claim 16, wherein n is the number 1; L$^1$ and L$^2$ are hydrogen; T is hydrogen or methyl; X$^1$ and X$^2$ are m-chlorophenyl; Y is 2-phenethoxyethyl or 2-ethoxyethyl: wherein the C-atom to which X$^1$ is attached has the R-configuration and the C-atom to which X$^2$ is attached has the R- or S-configuration.

28. A composition according to claim 16 wherein said active compound is α,α'-[[[p-(2-Ethoxyethoxy)phenethyl]imino]-dimethylene]bis[(R)-m-chlorobenzyl alcohol].

29. A composition according to claim 16, wherein said active compound is selected from the group consisting of;

α,α'-[[[(R)-α-Methyl-p-[2-(phenethoxy)ethoxy]-phenethyl]imino]dimethylene]bis[(R)-m-chlorobenzyl alcohol], (R)-m-chloro-α-[[[(S)-m-chloro-β-hydroxyphenethyl](R)-α-methyl-p-[2-(phenethoxy)ethoxy]-phenethyl]amino]methyl]benzyl alcohol, 3-chloro-α,α'-[[[(R)-p-(2-ethoxyethoxy)-α-methylphenethyl]imino]dimethylene]di-(R)-benzyl alcohol, (S)-m-chloro-α-[[[(R)-p-(2-ethoxyethoxy)-α-methylphenethyl][(R)-β-hydroxyphenthyl]amino]methyl]-benzyl alcohol, (R)-m-chloro-α-[[[(S)-m-chloro-β-hydroxyphenethyl][p-(2-ethoxyethoxy)phenethyl]amino]methyl]-benzyl alcohol and (R)-m-chloro-α-[[[(S)-m-chloro-β-hydroxyphenethyl][p-(2-phenethoxyethoxy)phenethyl]amino]methyl]benzyl alcohol.

30. A composition according to claim 16, wherein said carrier is a solid material.

31. A composition according to claim 16 wherein said carrier is an aqueous liquid or oily material.

32. A method for treating a subject suffering from obese adult diabetes, which method comprises administering to said subject a therapeutically effective amount a compound of the formula

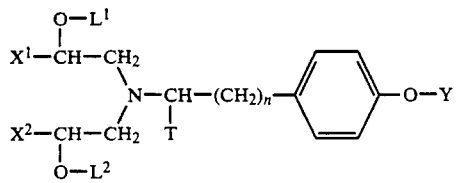

wherein n is the number 1 or 2; $L^1$ and $L^2$ are hydrogen, $C_{1-3}$-(alkyl)carbonyl or $C_{1-3}$ (alkoxy)carbonyl; T is hydrogen or methyl; $X^1$ and $X^2$ are phenyl or phenyl which is monosubstituted in the m-position by Br, Cl, F, $CF_3$ or $NO_2$; Y is —$(CH_2)_{1-6}$—O—G, —$(CH_2)_{1-6}$—CH=CH—C(O)—Z, —C(O)—Z or —CH(COOR'')_2$; G is $C_{1-4}$-alkyl, $C_{1-4}$-alkoxy-$C_{1-4}$-alkyl or —$(CH_2)_{1-4}$—Q; Q is phenoxy, phenyl, p-fluorophenyl or p-phenoxyphenyl; Z is a -OR or -N(R,R'): R and R' are hydrogen or $C_{1-4}$-alkyl or R and R' together with the N-atom to which they are attached form a 5- or 6-membered saturated ring which optionally contains an O-atom or an additional N-atom: and R'' is $C_{1-4}$-alkyl; as well as the physiologically compatible salts thereof.

33. A method according to claim 32 wherein said compound is selected from the group consisting of α,α'-[[[(R)-α-Methyl-p-[2-(phenethoxy)ethoxy]-phenethyl]imino]dimethylene]bis[(R)-m-chlorobenzyl alcohol], (R)-m-chloro-α-[[[(S)-m-chloro-β-hydroxyphenethyl]-(R)-α-methyl-p-[2-(phenethoxy)ethoxy]-phenethyl]amino]methyl]benzyl alcohol, 3-chloro-α,α'-[[[(R)-p-(2-ethoxyethoxy)-α-methylphenethyl]imino]dimethylene]di-(R)-benzyl alcohol, (S)-m-chloro-α-[[[(R)-p-(2-ethoxyethoxy)-α-methylphenethyl][(R)-β-hydroxyphenethyl]amino]methyl]-benzyl alcohol, (R)-m-chloro-α-[[[(S)-m-chloro-β-hydroxyphenethyl][p-(2-ethoxyethoxy)phenethyl]amino]methyl]-benzyl alcohol and (R)-m-chloro-α-[[[(S)-m-chloro-β-hydroxyphenethyl][p-(2-phenethoxyethoxy)phenethyl]amino]methyl]benzyl alcohol, and α,α'-[[[p-(2-Ethoxyethoxy)phenethyl]imino]-dimethylene]bis[(R)-m-chlorobenzyl alcohol].

34. A method according to claim 32, wherein said compound is

α,α'-[[p-(2-Ethoxyethoxy)phenethyl]imino]-dimethylene]bis[(R)-m-chlorobenzyl alcohol].

* * * * *